US005692508A

United States Patent [19]

Simonetti et al.

[11] Patent Number: 5,692,508
[45] Date of Patent: Dec. 2, 1997

[54] CARDIAC-GATED 3-DIMENSIONAL MR ANGIOGRAPHY

[75] Inventors: Orlando P. Simonetti, High Bridge; J. Paul Finn, Cranbury, both of N.J.

[73] Assignee: Siemens Medical Systems, Inc., Iselin, N.J.

[21] Appl. No.: 632,256

[22] Filed: Apr. 15, 1996

[51] Int. Cl.$^6$ .................................................. A61B 5/55
[52] U.S. Cl. .................................. 128/653.3; 128/653.4
[58] Field of Search ........................... 128/653.2, 653.3, 128/653.4

[56] References Cited

U.S. PATENT DOCUMENTS

| | | | |
|---|---|---|---|
| 5,167,232 | 12/1992 | Parker et al. | 128/653.3 |
| 5,190,744 | 3/1993 | Rocklage et al. | 128/653.3 |
| 5,285,158 | 2/1994 | Mistretta et al. | 128/653.3 |

Primary Examiner—Marvin M. Lateef
Assistant Examiner—Derrick Fields
Attorney, Agent, or Firm—Mark H. Jay

[57] ABSTRACT

A three-dimensional gadolinium-enhanced MR study of e.g. the patient's thoracic vasculature is carried out while the patient holds his or her breath. Acquisition of all data in each three-dimensional partition takes place during one and only one heartbeat. By synchronizing the MR pulse sequence to the patient's cardiac cycle, and advantageously by acquiring the MR data during the diastolic phase of the cardiac cycle, image artifacts caused by cardiac motion and pulsatile flow are eliminated or minimized.

7 Claims, 2 Drawing Sheets

CARDIAC-GATED 3-DIMENSIONAL MR ANGIOGRAPHY

BACKGROUND OF THE INVENTION

The invention relates to magnetic resonance (MR) imaging, and more particularly relates to contrast-enhanced MR angiography (MRA). In its most immediate sense, the invention relates to gadolinium-enhanced three-dimensional ECG-triggered MR angiography.

In gadolinium-enhanced MRA, a gadolinium contrast agent (typically Gd-DTPA) is introduced into the patient's bloodstream and an MR study is conducted while the patient holds his or her breath. While the breath hold causes respiratory motion to cease, image artifacts can arise from other types of motion. For example, cardiac motion and pulsatile flow of blood can generate artifacts in thoracic vessels near the heart and in small cardiac vessels. These artifacts are evident in three-dimensional gadolinium-enhanced MRA.

Accordingly, one object of the invention is to provide a method of carrying out a three-dimensional MRA study in which e.g. cardiac motion and pulsatile flow in the patient's cardiac vessels do not introduce artifacts into the image.

In accordance with the invention, a three-dimensional MR pulse sequence is gated to the patient's cardiac cycle. In further accordance with the invention, the gating is so carried out during the study that the number of three-dimensional partitions in the study equals the number of heartbeats taking place during the study, and acquisition of all MR data in each partition takes place during one and only one heartbeat. Advantageously, a gadolinium contrast agent is used during the study, while the patient holds his or her breath.

Because the pulse sequence is synchronized with the patient's cardiac cycle, cardiac motion and pulsatile flow do not cause image artifacts. Advantageously, data acquisition does not commence at the very beginning of a cardiac cycle; data acquisition starts only after a short delay. This causes the MR data to be collected during the diastolic phase of the cardiac cycle, avoiding the cardiac motion and rapid changes in blood velocity that take place during the systolic phase.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
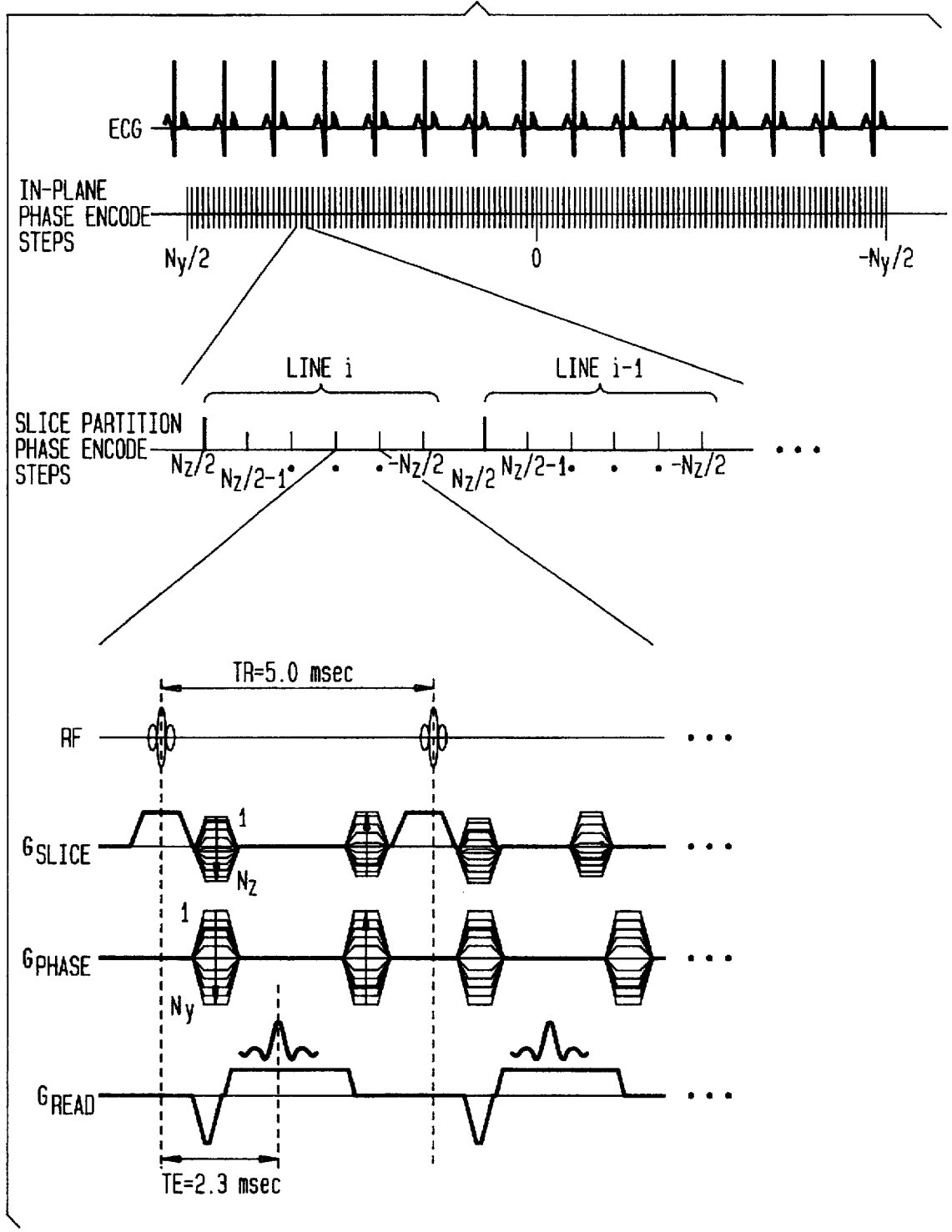
FIG. 1 is a diagram of a three-dimensional MR pulse sequence of the type conventionally used in a gadolinium-enhanced MR study of a patient's thoracic vasculature.

In a conventional gadolinium-enhanced three-dimensional MRA study of a patient's thoracic vasculature, an MR pulse sequence such as FIG. 1 is utilized. FIG. 1 illustrates a known three-dimensional RF-spoiled gradient echo pulse sequence having a TR per line of 5 msec, a TE equalling 2.3 msec, a readout bandwidth of 488 Hz/pixel, and no gradient moment nulling. Typically, there are 96–256 in-plane phase-encode lines and 16–32 partitions having a partition thickness from 1 mm to 4 mm, the flip angle ranges from 15° to 30°, and the field of view is between 250 mm$^2$ to 400 mm$^2$. In this type of sequence, for each in-plane phase-encoding step, one line of MR data is read out from each of the three-dimensional partitions in order. This is repeated until a complete three-dimensional MR data set has been acquired. Data acquisition is not synchronized with respect to the cardiac cycle.

Figure 2:
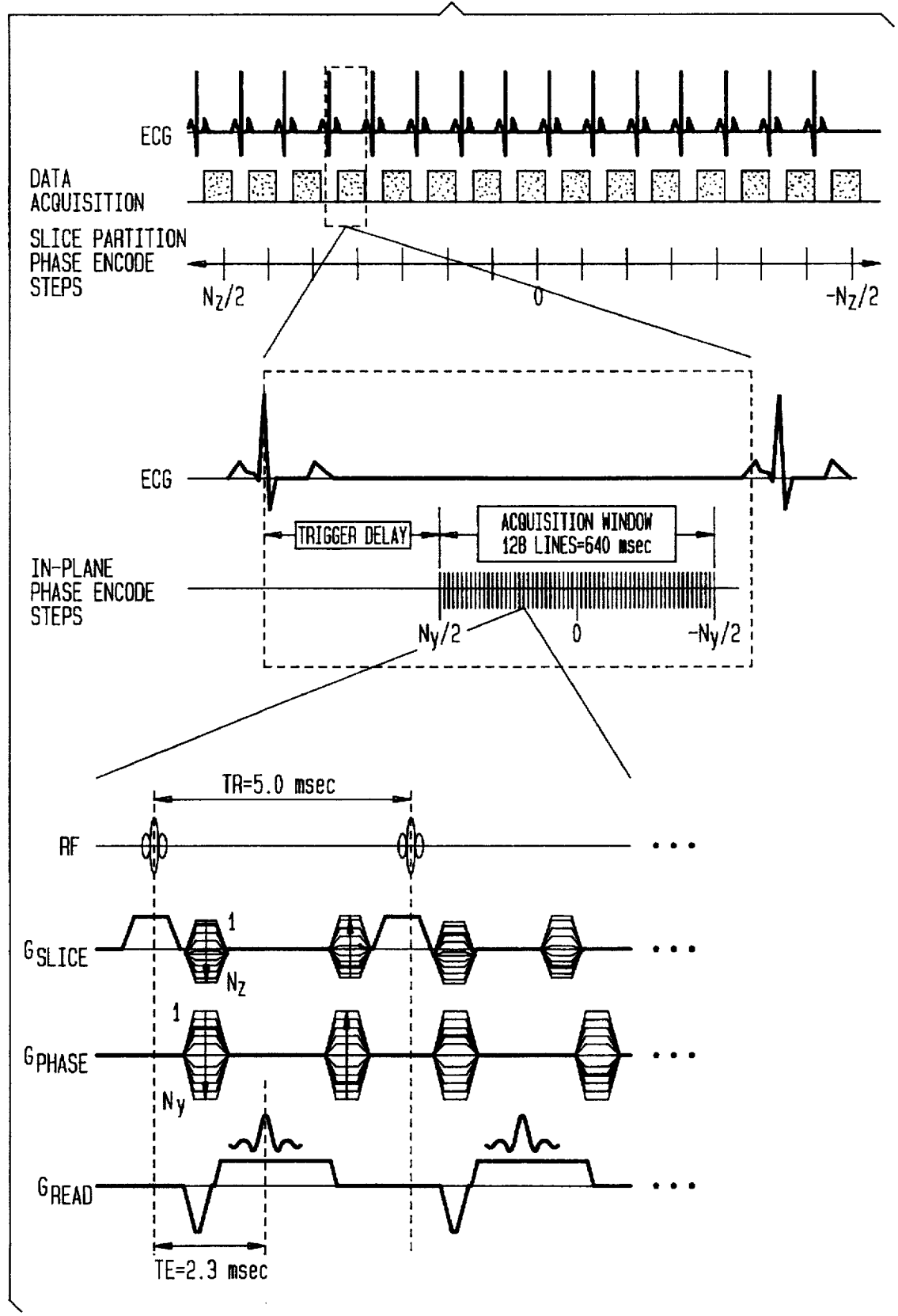
FIG. 2 is a diagram of an MR pulse sequence in accordance with the preferred embodiment of the invention.

In accordance with the preferred embodiment of the invention as used in a thoracic MRA study, an MR pulse sequence such as is illustrated in FIG. 2 is utilized to image the patient's thorax after administration of Gd-DPTA. In this instance as well, the sequence has a TR per line of 5 msec, a TE equalling 2.3 msec, a readout bandwidth of 488 Hz/pixel, and no gradient moment nulling. Likewise, there are typically 96–256 in-plane phase-encode lines and 16–32 partitions having a partition thickness from 1 mm to 4 mm, the flip angle ranges from 15° to 30°, and the field of view is between 250 mm$^2$ to 400 mm$^2$. However, in accordance with the preferred embodiment of the invention, this MR pulse sequence is gated to the patient's cardiac cycle and the MR data is acquired in a different order.

In accordance with the preferred embodiment of the invention, the gating is so carried out during the study that the number of three-dimensional partitions in the study equals the number of heartbeats taking place during the study. Furthermore, acquisition of all MR data in each partition takes place during one and only one heartbeat.

Immediately after administration of Gd-DTPA (at a dose of 0.1 or 0.2 mmol/kg of body weight as a bolus over approximately 10 seconds) to the patient's circulatory system, and after the beginning of the patient's cardiac cycle is determined by detection of an R-wave, there is a delay. (The delay is between 0 and 300 msec, and is typically approximately 200 msec.) Then, the FIG. 2 MR pulse sequence is initiated to commence acquisition of all MR data from one three-dimensional partition. This data acquisition is carried out sufficiently quickly that it is concluded before the end of the patient's cardiac cycle, i.e. all MR data is acquired from a single three-dimensional partition during one and only one heartbeat. Although the delay between the R-wave and the start of data acquisition is not necessary, it is preferred because this causes the MR data to be read out during the diastolic phase of the cardiac cycle rather than during the systolic phase (when cardiac motion is maximal and when the rate of bloodflow changes greatly). This process is then repeated, once per heartbeat, for all the partitions (all the heartbeats) in the study.

Each acquisition takes place during a window of 500–700 msec. During this time, the in-plane phase-encoding gradients are varied linearly from one extremum to the other. Typically, there are between 96 and 140 such phase encodings for each partition.

This process is repeated once per heartbeat as many times as there are heartbeats during the study, while the patient holds his or her breath. Typically, a breath hold will last 15 to 30 seconds. In the typical instance, MR data for 16 to 32 slice partitions will be acquired during a thoracic study, each slice being between 2 and 3 mm thick.

Although a preferred embodiment has been described above, the scope of the invention is limited only by the following claims:

We claim:

1. A method of carrying out a three-dimensional MRA study of a patient, comprising:
    gating a three-dimensional MR pulse sequence to the patient's cardiac cycle in a manner that the number of three-dimensional partitions in the study equals the number of heartbeats taking place during the study, and acquisition of all MR data in each partition takes place during one and only one heartbeat.

2. The method of claim 1, further comprising the step of administering a contrast agent into the patient's vascular system before acquiring MR data.

3. The method of claim 2, wherein the agent is a chemical compound that includes gadolinium.

4. The method of claim 1, wherein said study is carried out while the patient is holding the patient's breath.

5. The method of claim 1, wherein acquisition of MR data in each partition is commenced only after a predetermined delay interval after the beginning of the cardiac cycle, whereby all MR data in each partition is acquired during diastole.

6. The method of claim 1, wherein the study is of the patient's peripheral vasculature.

7. A method of carrying out a three-dimensional MRA study of a patient's thoracic vasculature, comprising:

gating a three-dimensional MR pulse sequence to the patient's cardiac cycle in a manner that the number of three-dimensional partitions in the study equals the number of heartbeats taking place during the study, and acquisition of all MR data in each partition takes place during one and only one heartbeat;

administering a contrast agent into the patient's vascular system; and running said MR pulse sequence on an MR imager and acquiring MR data from the patient's thoracic vasculature.

* * * * *